United States Patent
Brodkin et al.

(10) Patent No.: US 9,585,736 B2
(45) Date of Patent: *Mar. 7, 2017

(54) DENTAL ARTICLES USING NANOCRYSTALLINE MATERIALS AND METHODS OF MANUFACTURE

(71) Applicant: Ivoclar Vivadent AG, Schaan (LI)

(72) Inventors: Dmitri Brodkin, Livingston, NJ (US); Moisey Y. Gamarnik, Warminster, PA (US)

(73) Assignee: Ivoclar Vivadent AG, Schaan (LI)

( * ) Notice: Subject to any disclaimer, the term of this patent is extended or adjusted under 35 U.S.C. 154(b) by 296 days.

This patent is subject to a terminal disclaimer.

(21) Appl. No.: 14/258,413

(22) Filed: Apr. 22, 2014

(65) Prior Publication Data
US 2014/0300013 A1    Oct. 9, 2014

Related U.S. Application Data

(62) Division of application No. 13/182,210, filed on Jul. 13, 2011, now Pat. No. 8,741,050, which is a division
(Continued)

(51) Int. Cl.
*B22F 3/12*    (2006.01)
*A61C 13/08*    (2006.01)
(Continued)

(52) U.S. Cl.
CPC ........ *A61C 13/081* (2013.01); *A61C 13/0006* (2013.01); *A61C 13/083* (2013.01);
(Continued)

(58) Field of Classification Search
None
See application file for complete search history.

(56) References Cited

U.S. PATENT DOCUMENTS

| | | |
|---|---|---|
| 4,265,669 A | 5/1981 | Staring et al. |
| 4,360,598 A | 11/1982 | Otagiri et al. |

(Continued)

FOREIGN PATENT DOCUMENTS

WO    02/074714 A1    9/2002

OTHER PUBLICATIONS

Wang, Z.L., et al., Shape Transformation and Surface Melting of Cubic and Tetrahedral Platinum Nanocrystals, The Journal of Physical Chemistry B, vol. 102, No. 32, Aug. 6, 1998, pp. 6145-6151.

(Continued)

*Primary Examiner* — Jessee Roe
*Assistant Examiner* — Ngoclan T Mai
(74) *Attorney, Agent, or Firm* — Ann M. Knab; Thad McMurray

(57) ABSTRACT

Method of forming dental articles by using relatively low sintering temperatures to achieve high density dental articles exhibiting strengths equal to and greater than about 700 MPa. Ceramic powders comprised of nanoparticulate crystallites are used to manufacture dental articles. The ceramic powders may include sintering agents, binders and other similar additives to aid in the processing of the ceramic powder into a dental article. The ceramic powders may be processed into dental articles using various methods including, but not limited to, injection molding, gel-casting, slip casting, or electroforming, hand, cad/camming and other various rapid prototyping methods. The ceramic powder may be formed into a suspension, pellet, feedstock material or a pre-sintered blank prior to forming into the dental article.

15 Claims, 4 Drawing Sheets

Related U.S. Application Data of application No. 12/872,685, filed on Aug. 31, 2010, now Pat. No. 8,002,885, which is a division of application No. 12/490,539, filed on Jun. 24, 2009, now Pat. No. 7,806,694, which is a division of application No. 10/857,482, filed on May 28, 2004, now Pat. No. 7,655,586.

(60) Provisional application No. 60/474,166, filed on May 29, 2003.

(51) Int. Cl.

| | |
|---|---|
| A61C 13/00 | (2006.01) |
| A61C 13/083 | (2006.01) |
| C01G 25/00 | (2006.01) |
| C04B 35/486 | (2006.01) |
| C04B 35/626 | (2006.01) |
| C04B 35/632 | (2006.01) |
| C04B 35/645 | (2006.01) |
| B82Y 30/00 | (2011.01) |
| B22F 3/22 | (2006.01) |
| B22F 3/14 | (2006.01) |

(52) U.S. Cl.
CPC .............. *B82Y 30/00* (2013.01); *C01G 25/00* (2013.01); *C04B 35/486* (2013.01); *C04B 35/62695* (2013.01); *C04B 35/632* (2013.01); *C04B 35/645* (2013.01); *B22F 3/12* (2013.01); *B22F 3/14* (2013.01); *B22F 3/22* (2013.01); *B22F 3/225* (2013.01); *C01P 2004/64* (2013.01); *C04B 2235/3206* (2013.01); *C04B 2235/3217* (2013.01); *C04B 2235/3225* (2013.01); *C04B 2235/3229* (2013.01); *C04B 2235/3232* (2013.01); *C04B 2235/3241* (2013.01); *C04B 2235/3246* (2013.01); *C04B 2235/3251* (2013.01); *C04B 2235/3262* (2013.01); *C04B 2235/3279* (2013.01); *C04B 2235/3418* (2013.01); *C04B 2235/5409* (2013.01); *C04B 2235/549* (2013.01); *C04B 2235/5427* (2013.01); *C04B 2235/5436* (2013.01); *C04B 2235/5454* (2013.01); *C04B 2235/5472* (2013.01); *C04B 2235/604* (2013.01); *C04B 2235/6022* (2013.01); *C04B 2235/6023* (2013.01); *C04B 2235/6026* (2013.01); *C04B 2235/6027* (2013.01); *C04B 2235/612* (2013.01); *C04B 2235/6562* (2013.01); *C04B 2235/6565* (2013.01); *C04B 2235/667* (2013.01); *C04B 2235/668* (2013.01); *C04B 2235/77* (2013.01); *C04B 2235/785* (2013.01); *C04B 2235/94* (2013.01); *C04B 2235/9615* (2013.01); *C04B 2235/9653* (2013.01)

(56) References Cited

U.S. PATENT DOCUMENTS

| | | |
|---|---|---|
| 4,585,417 A | 4/1986 | Sozio et al. |
| 4,772,436 A | 9/1988 | Tyszblat |
| 4,788,045 A | 11/1988 | Colombet et al. |
| 4,820,666 A | 4/1989 | Hirano et al. |
| 4,977,114 A | 12/1990 | Horinouchi et al. |
| 5,223,186 A | 6/1993 | Eastman et al. |
| 5,248,463 A | 9/1993 | Obitsu et al. |
| 5,419,827 A | 5/1995 | Nanataki et al. |
| 5,667,548 A | 9/1997 | Graule et al. |
| 5,788,891 A | 8/1998 | Gauckler et al. |
| 5,849,068 A | 12/1998 | Hofmann et al. |
| 5,863,850 A | 1/1999 | Nawa et al. |
| 5,910,273 A | 6/1999 | Thiel et al. |
| 5,916,498 A | 6/1999 | Hofmann et al. |
| 5,948,335 A | 9/1999 | Gauckler et al. |
| 5,955,392 A | 9/1999 | Takeuchi et al. |
| 5,975,905 A | 11/1999 | Kim et al. |
| 6,013,591 A | 1/2000 | Ying et al. |
| 6,059,949 A | 5/2000 | Gal-Or et al. |
| 6,066,584 A | 5/2000 | Krell et al. |
| 6,087,285 A | 7/2000 | Oomichi et al. |
| 6,126,732 A | 10/2000 | Hofmann et al. |
| 6,287,121 B1 | 9/2001 | Guiot et al. |
| 6,322,728 B1 | 11/2001 | Brodkin et al. |
| 6,506,054 B2 | 1/2003 | Shoher et al. |
| 6,641,775 B2 | 11/2003 | Vigliotti et al. |
| 6,669,476 B2 | 12/2003 | Prestipino et al. |
| 6,691,764 B2 | 2/2004 | Embert et al. |
| 6,730,156 B1 * | 5/2004 | Windisch ............ A61K 6/0017 106/35 |
| 6,808,659 B2 | 10/2004 | Schulman et al. |
| 6,821,462 B2 | 11/2004 | Schulman et al. |
| 6,994,549 B2 | 2/2006 | Brodkin et al. |
| 7,162,321 B2 | 1/2007 | Luthardt et al. |
| 2002/0006532 A1 | 1/2002 | Robin |
| 2004/0043204 A1 * | 3/2004 | Nair ...................... C04B 35/111 428/212 |

OTHER PUBLICATIONS

Castro, T., et al., Size-dependent melting temperature of individual nanometer-sized metallic clusters, Physical Review B, The American Physical Society, vol. 42, No. 13, Nov. 1, 1990, pp. 8548-8556.

Lee, et al., Size-Controlled Synthesis of Pd Nanowires Using a Mesoporous Silica Template via Chemical Vapor Infiltration, Adv. Mater., Apr. 4, 2001, vol. 13, No. 7, pp. 517-520.

Lai, S.L., et al., Size-Dependent Melting Properties of Small Tin Particles: Nanocalorimetric Measurements, Physical Review Letters, vol. 77, No. 1, Jul. 1, 1996, The American Physical Society, pp. 99-102.

Goldstein, A.N., et al., Melting Semiconductor Nanocrystals, Science, vol. 256, Jun. 5, 1992, pp. 1425-1427.

Wu, Y., et al., Melting and Welding Semiconductor Nanowires in Nanotubes, Adv. Mater., Apr. 4, 2001, vol. 13, No. 7, pp. 520-523.

Kimel, R.A., Aqueous Synthesis and Processing of Nanosized Yttha Tetragonally Stabilized Zirconia, A Thesis in Materials Science and Engineering, The Pennsylvania State University, The Graduate School College of Earth and Mineral Sciences, Aug. 2002, pp. 1-111.

CAD/CAM Dossier, CAD/CAM Opportunity or Threat?, Dental Technologies, No. 25, Jul. 2001, pp. 5-23.

Peters, K.F., et al., Melting of Pb Nanocrystals, Physical Review B, The American Physical Society, vol. 57, No. 21, Jun. 1, 1998, pp. 430-438.

Zorzi, J.E., et al., Wax-based binder for low-pressure injection molding and the robust production of ceramic parts, Industrial Ceramics, vol. 23, No. 1, Jan.-Mar. 2003, pp. 1-13.

Couchman, P.R., et al., Thermodynamic theory of size dependence of melting temperature in metals, Nature vol. 269, Oct. 6, 1997, pp. 481-483.

Wronski, C.R.M., The Size Dependence of the Melting Point of Small Particles of Tin, British Journal of Applied Physics, 1967, vol. 18, pp. 1731-1737.

Bachels, T., et al., Melting of Isolated Tin Nanoparticles, Physical Review Letters, vol. 85, No. 6, Aug. 7, 2000, pp. 1250-1253.

Gamarnik, M,Y., Size Dependence of the Specific Energy of Crystals, Sov. Phys. Solid State 31(1 ), Jan. 1989, The American Institute of Physics, pp. 126-129.

Zhang, Z, et al., Modelling for Size-Dependent and Dimension-Dependent Melting of Nanocrystals, J. Phys. D: Appl. Phys., vol. 33, No. 20, Oct. 21, 2000, pp. 2653-2656.

Zhang, Z., et al., Melting Temperatures of Semiconductor Nanocrystals in the Mesoscopic Size Range, Institute of Physics Publishing, Semicond. Sci. Technol., vol. 16, No. 6, Jun. 2001, pp. L33-L35.

(56) References Cited

OTHER PUBLICATIONS

Shi, F.G., Size Dependent Thermal Vibrations and Melting in Nanocrystals, J. Mater, Res., vol. 9, No. 5, May 1994, pp. 1307-1313.

Qi, Y., et al., Melting and Crystallization in Ni Nanoclusters: The Mesoscale Regime, Journal of Chemical Physics, vol. 115, No. 1, Jul. 1, 2001, pp. 385-394.

Inagaki, Y., et al., Fracture Energy of an Aligned Porous Silicon Nitride, J. Am. Ceram. Soc, vol. 83, No. 7, Jul. 2000, pp. 1807-1809.

Skandan, G., et al., Ultrafine-Grained Dense Monoclinic and Tetragonal Zirconia, J. Am. Ceram. Soc, vol. 77, No. 7, 1994, pp. 1706-1710.

Filser, F., et al., All-Ceramic Dental Bridges by the Direct Ceramic Machining (DCM), Bioceramics, vol. 10, Proceedings of the 10th International Symposium on Ceramics in Medicine, Paris, France, Oct. 1997, pp. 433-436.

Barsoum, M.W., Fundamentals of Ceramics, 1997, pp. 616, 634-637, McGraw-Hill, US.

3M ESPE Lava Frame—Zirconia Crown/Bridge Mill Blanks, Instruction for Use, 3M ESPE Dental Products 2006.

Ban, S., Review Article—Reliability and properties of core materials for all-ceramic dental restorations, Japanese Dental Science Review, Jul. 2008, vol. 44, No. 1, pp. 3-21. www.sciencedirect.com.

Nano, ultrafine and submicron grades, www.allaboutcementedcarbide.com, 2008.

Zheng, et al., "Cyclic Behavior and Room Temperature Micromechanism of 3Y-TZP Ceramics at Submicron and Nanocrystalline Levels," Wiley InterScience, Apr. 10, 1996 (Abstract).

\* cited by examiner

DENTAL ARTICLES USING NANOCRYSTALLINE MATERIALS AND METHODS OF MANUFACTURE

CROSS-REFERENCE TO RELATED APPLICATIONS

This application is a divisional application and claims priority to U.S. application Ser. No. 13/182,210, filed Jul. 13, 2011, entitled Dental Restorations Using Nanocrystalline Materials, now U.S. Pat. No. 8,741,050, which is a divisional application of U.S. application Ser. No. 12/872,685 filed Aug. 31, 2010, entitled Dental Restorations Using Nanocrystalline Materials, now U.S. Pat. No. 8,002,885, which is a divisional application of and claims priority to U.S. application Ser. No. 12/490,539, filed Jun. 24, 2009, entitled Methods of Manufacturing Dental Restorations Using Nanocrystalline Materials, now U.S. Pat. No. 7,806,694, which is a divisional application of and claims priority to U.S. application Ser. No. 10/857,482, filed May 28, 2004, entitled Dental Restorations Using Nanocrystalline Materials and Methods of Manufacture, now U.S. Pat. No. 7,655,586, which claims priority to U.S. Application No. 60/474,166 filed May 29, 2003, entitled Methods of Fabricating Dental Restorations Using Nanocrystalline Materials, all of which are hereby incorporated by reference.

FIELD OF THE INVENTION

This invention relates to nanocrystalline ceramic powders especially useful for fabricating dental restorations and methods of fabricating dental restorations using ceramic powders comprising nanoparticles.

BACKGROUND OF THE INVENTION

Techniques of fabricating all-ceramic dental restorations by hand and methods using commercial high-tech systems such as CAD/CAM systems each have their limitations and target different segments of the dental laboratory market. There are two main challenges restricting widespread use of high-strength ceramic materials for cost-effective fabrication of dental restorations and both challenges are related to the sintering step of the operation. High-strength ceramic materials are crystalline materials formed from powder and require high temperatures for sintering that result in substantial shrinkage. Any technique enabling use of these materials for dental restorations should offer ways to (1) compensate for shrinkage and (2) provide a furnace capable of reaching the temperatures necessary to sinter the material to nearly full density.

A technique reportedly providing the highest strength for manually produced copings, the Vita® In-Ceram™ method (developed by VITA Zahnfabrik), has been advertised as yielding a material with flexural strength of about 500 MPa or even higher. This technique has not become popular mostly due to esthetic limitations and a tedious multi-step fabrication procedure that includes a glass infiltration step. This glass infiltration technique is one way to circumvent the above-mentioned challenges. Vita® In-Ceram™ copings are slip-cast on a gypsum die and soft-sintered with negligible shrinkage. The final glass infiltration step does not require a special furnace. The resulting product is a fully dense restoration having undergone no shrinkage. Nonetheless, the presence of a glass phase in the glass-infiltrated ceramics makes it inferior to corresponding crystalline ceramics in mechanical strength and chemical durability.

Currently available CAD/CAM systems are capable of compensating for shrinkage by milling enlarged shapes. Moreover, high-temperature isotropic sintering results in fully dense and accurate final shapes. However, CAD/CAM systems and procedures are expensive and not affordable by small labs. For example, two of the most recently developed commercial state-of-the art CAD/CAM systems, the LAVA™ system (available from 3M ESPE) and the CERCON® system (available from Dentsply/Degussa), require the purchase of a scanner, milling machine and high-temperature sintering furnace and are currently priced in the range of approximately $60,000-$180,000. Both of the aforementioned CAD/CAM systems employ soft-sintered zirconia blocks. The blocks are milled to enlarged shapes and subsequently sintered to full density. Both systems are advertised as yielding materials having a flexural strength of about 900 MPa or higher.

Glass-ceramic materials obviate the need to compensate for shrinkage and high temperature sintering. They can be hand-built on a refractory die and sintered at fairly low temperatures to assure accuracy of the final shape. One example of such a material is an OPC™ Low Wear (available from Pentron Laboratory Technologies, LLC) porcelain jacket crown (PJC). Glass-ceramic materials can also be injection molded into a refractory investment mold formed by the lost wax technique. Examples of commercially available materials used in this process include OPC® porcelain, and OPC® 3™ porcelain, IPS Empress® porcelain and Empress 2™ porcelain. The physical mechanism underlying the high processability/formability of these glass-ceramics is the viscous flow of its glass component. The glass-ceramic materials listed above (Optec™ OPC® and OPC® 3G™, Empress® and Empress2™ materials) have from about 40% to about 60% of a glass phase which serves as a matrix in which from about 40% (e.g., Optec) to about 60% of crystals (e.g., Empress2) are embedded. These crystals are grown in-situ by crystallisation heat-treatment of the parent glass. Alternatively, in a method described by Hoffman in U.S. Pat. Nos. 5,916,498, 5,849,068 and 6,126,732, in order to improve processability of the material, up to 50% glass is added to the crystalline ceramic powder. As a result, the reported flexure strength is limited to less than 600 MPa. By introducing a glass phase into the microstructure, strength is compromised to gain better processability.

Sintering of glass-ceramic powders is a relatively fast process compared to sintering of crystalline ceramic powders due to the viscous flow mechanism of the former, which is associated with higher densification rates, but the presence of the residual glass phase limits the strength of the final product. Another benefit of the viscous flow mechanism is that the glass ceramic conforms to the shape of the die during sintering without cracking. On the other hand, crystalline ceramics can be much stronger than glass ceramics, but crystalline ceramics sinter by a solid-state diffusion mechanism that is intrinsically slow creating inhomogeneous shrinkage, generating significant sintering stresses that may result in associated cracking. Liquid phase sintering induced by the addition of sintering aids greatly enhances sinterability of crystalline ceramics by promoting particle rearrangement and solution-precipitation mechanisms but such mechanisms do not achieve all the advantages of the viscous flow mechanism.

At the same time many experimental and theoretical studies reveal a decrease of the melting temperature of nanometallic particles in comparison with the melting temperature of conventional bulk metals. Its magnitude depends mostly on particle size and crystal structure as well as particle surface conditions and the host matrix environment such as the presence of impurities, level of agglomeration, coating, deposition substrate and the like. Usually, melting is associated with a pre-melting process resulting in a change in shape of the nanoparticles followed by the formation of a liquid skin on the melting nanoparticles. The liquid skin thickness increases during melting gradually consuming the solid particle core. Transmission electron microscopy studies, such as the one discussed in "Shape Transformation and Surface Melting of Cubic and Tetrahedral Platinum Nanocrystals" by Z. L. Wang, J. M. Petroski, T. C. Green and M. A. El-Sayed, *J. Phys. Chem.* 102, (32) 6145-6151 (1998), have established that 8 nanometer platinum nanoparticles begin to melt at about 600° to about 650° C., which is a much lower temperature than the melting point of bulk platinum at 1769° C. At about 500° C., cubic particles change their shape to a spherical shape with surface melting occurring at about 600° C. to about 650° C. The molten layer surrounding solid cores of platinum nanocrystals is about 1 nm in thickness at 600° C. and the thickness increases with temperature as the nanoparticles continue to melt. The "melting point depression" abbreviated as MPD is a thermodynamically driven phenomenon and can be explained by a drastic increase in the surface area/volume ratio in nano-particulate materials and the corresponding increase in their specific surface energy. This leads to a size-related dependence of melting temperature that is roughly close to 1/d functionality, where d is the mean particle size, and contains surface tension coefficients, latent heat of melting and the molten skin thickness as parameters.

Table 1 presents some experimental data illustrating the difference in melting temperatures for nanoparticles and the corresponding bulk metals and semiconductors.

and hence facilitating densification at temperatures much lower than 0.6 of the melting point ($T_m$).

It can be further speculated that thermodynamic considerations explaining the mechanism of MPD described above should hold for ceramic nanoparticles as well. Nevertheless, the MPD effect is not very well studied in ceramics for obvious reasons—even the depressed melting point anticipated for ceramic nanoparticles will still be very high making it extremely difficult to conduct observations similar to those for metals and semiconductors described above in Table 1.

For example, the melting point ($T_M$) for pure alumina and zirconia are 2050° C. and 2700° C., respectively, and therefore the MPD effect of the order of $0.5 T_M$ will result in melting temperatures for nano-alumina and nano-zirconia particles of about 1025° C. and 1350° C. However, there are some indirect indications that MPD does occur in nanoceramics such as extremely low sintering temperatures for nanopowders as reported in R. A. Kimel, *Aqueous Synthesis and Processing of Nanosized Yttria Tetragonally Stabilised Zirconia*, Ph.D. Thesis, The Pennsylvania State University, the Graduate School, the College of Earth and Mineral Sciences, (2002) and in G. Skandan, H. Hahn, M. Roddy and W. R. Cannon, "Ultrafine-Grained Dense Monoclinic and Tetragonal Zirconia," J. Am. Ceram. Soc., vol. 77, no. 7, pp. 1706-10 (1994), which are both hereby incorporated by reference.

These studies reported onset of densification at surprisingly low temperatures of about $0.3 T_M$ as well as a surprising and unique ability of nanoceramics to be translucent at fairly high levels of porosity.

Some studies reported extreme difficulty in sintering nanoceramics to full density due to rapid grain growth. For

TABLE 1

Melting temperatures of the selected nanomaterials

| Material | Nano-Particle Shape | Nano-Particle size, nm | Nano-Material Melting Temperature ° C. | Bulk Melting Temperature ° C. | Melting Point Depression ° C. | $T_{Mnano}/T_{Mbulk}$ | Melting/Surface Melting | Ref. |
|---|---|---|---|---|---|---|---|---|
| Pt | cubic | 8 | 650 | 1769 | 1100 | 0.37 | surface melting | [1] |
| Au | spherical | 4 | 650 | 1057 | 400 | 0.61 | melting | [2] |
| Ag | spherical | 7 | 470 | 961 | 490 | 0.49 | melting | [2] |
| Pd | wire | Diameter 4.6 Length 202 | 300 | 1445 | 1100 | 0.21 | melting | [3] |
| Sn | spherical | 10 | 153 | 232 | 80 | 0.66 | melting | [4] |
| CdS | spherical | 4 | 630 | 1678 | 1080 | 0.38 | melting | [5] |
| Ge | wire | Diameter 55 Length 1000 | 650 | 930 | 280 | 0.70 | surface melting from ends | [6] |

[1] "Shape Transformation and Surface Melting of Cubic and Tetrahedral Platinum Nanocrystals." Z. L. Wang, J. M. Petroski, T. C. Green and M. A. El-Sayed, *J. Phys. Chem.* 102, (32), 6145-6151 (1998).
[2] "Size-Dependent Melting Temperature of Individual Nanometer-Sized Metallic Clusters," T. Castro, R. Reifenberger, E. Choi and R. P. Andres, *Phys. Rev.*, B 42 (13), 8548-8556 (1990).
[3] "Size Controlled Synthesis of Pd Nanowires Using a Mesoporous Silica Template Via Chemical Vapor Infiltrtion," K-B Lee, S-M Lee, and J. Cheou, *Adv. Mate.*, 13 (7), 517-520, (2001).
[4] "Size-Dependent Melting Properties of Small Tin Particles: Nanocalorimetric Measurement," S. L. Lai, J. Y. Guo, V. Petrova, G. Ramanath and L. H. Allen, *Phys. Rev. Lett.*, 77(1), 99-102, (1996).
[5] "Melting in Semiconductor Nanocrystals," A. N. Goldstein, C. M. Echer and A. P. Alivisatos, *Science*, 256, 1425-1427, (1992).
[6] "Melting and Welding Semiconductor Nanowires in Nanotuves," Y. Wu and P. Yang, *Adv. Mater.*, 13 (7), 520-523, (2001).

Onset of surface melting occurs usually at temperatures even lower than the temperature at which the entire nanoparticle melts. It can be speculated that the "molten shells" of the pre-melted nanoparticles work as "a lubricant" inducing higher mobility of the particles and higher diffusion rates example, Skandan et al. (cited above) observed that grains grew 15 times the initial particle size in the case of nano-zirconia. The other major obstacle encountered with the use of nanoparticles in the fabrication of dental articles is related to difficulties in the consolidating of bulk shapes using conventional methods like powder compaction and slip-casting. It the scope of the present invention to utilise the advantages of nanoparticulate ceramics while successfully overcoming the obstacles currently hampering use of such nanoparticulates as dental ceramics.

It is desirable to provide dental ceramics having low sintering temperatures and high strengths. It would be beneficial to provide dental ceramics having sintering temperatures that are low enough to be sintered in existing dental furnaces, yet maintaining high strength and translucency. It is most desirable to provide processing techniques for dental ceramics that result in fully densified dental ceramics.

SUMMARY OF THE INVENTION

These and other objects and advantages are accomplished by the ceramic powders of the present invention which are manufactured into dental articles. The ceramic powders may include sintering agents, binders and other similar additives to aid in the processing of the ceramic powder into a dental article. The ceramic powders are comprised of nanoparticulate crystallites. The ceramic powders may be processed into the dental article using various methods including, but not limited to, injection molding, gel-casting, slip casting, or electroforming, hand forming, cad/camming and other various rapid prototyping methods. The ceramic powder may be formed into a suspension, pellet, feedstock material or a pre-sintered blank prior to forming into the dental article.

Dental articles are produced using relatively low sintering temperatures to achieve high density dental articles exhibiting strengths equal to and greater than about 700 MPa.

BRIEF DESCRIPTION OF THE DRAWINGS

Features of the present invention are disclosed in the accompanying drawings, wherein similar reference characters denote similar elements throughout the several views, and wherein.

DETAILED DESCRIPTION OF THE INVENTION

This invention provides particulate materials that can be processed into dental restorations using both the most sophisticated state-of-the art technologies such as solid free form manufacturing (SFF) methods as set forth in U.S. Pat. No. 6,322,728, and copending commonly owned U.S. patent application Ser. No. 09/972,351 (US 2002/00335458), now U.S. Pat. No. 6,994,549, Ser. No. 10/053,430 (US 2002/0125592), now U.S. Pat. No. 6,808,659, and Ser. No. 09/946,413 (US 2002/0064745), now U.S. Pat. No. 6,821,462, all of which are hereby incorporated by reference, as well as manual techniques similar to classic methods of building porcelain jacket crowns on a refractory die (e.g. OPC™ Low Wear porcelain jacket crowns made from powder or jacket crowns made using tape-cast ceramic sheets as described in U.S. Pat. No. 5,975,905, which is hereby incorporated by reference) or slip casting a ceramic slip onto a porous die/mold.

Figure 1:
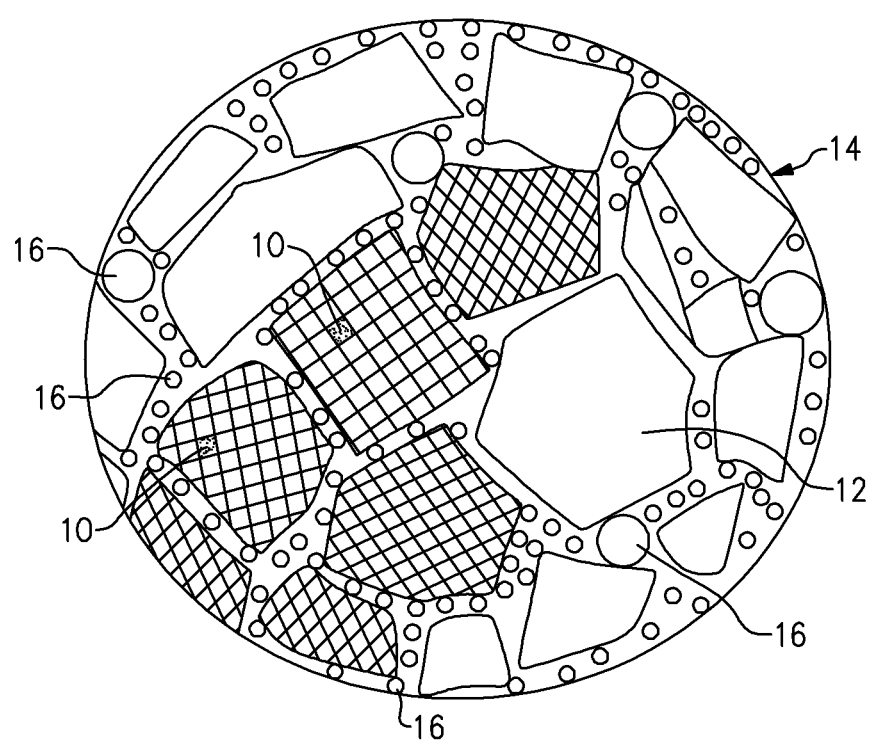
FIG. 1 is a schematic diagram showing the structure of particles described herein.

The ceramic particulate materials of the present invention have complex hierarchical architecture with three levels of structural organization: nano-, micro-, and macro-level as shown in FIG. 1. On the nano-level (≤20 nm), the structure is based on nano-crystallites depicted at 10 as elemental building blocks. On the micro-level (0.1-20 microns), the structure is formed from polycrystalline particles or agglomerates comprised of clusters of nanocrystallites depicted at 12. On a macro-level (20-200 microns), polycrystalline particles are agglomerated into granules depicted at 14. These granules 14 are made by spray-drying or fluidized bed agglomerating polycrystalline particles comprised of nanoparticles of one or more kinds of materials including, but not limited to, metallic and ceramic materials which may be fully or partially calcined or still in the form of organic/inorganic precursors. Sintering aids are depicted interstially at 16. The advantage of using nanoparticles is their drastically different sintering behavior associated with MPD. In much of the scientific literature, such as in, "Melting of Isolated Tin Nanoparticles" by T. Bachels, H-J Guntherodt, and R. Schafer, *Phy. Rev. Lett.*, 85, (6), 1250-1253, (2000), which is hereby incorporated by reference, this effect is also referred to as "size dependence of melting temperature" in nano-materials. As a result of this mechanism, sintering of nanoparticles is speculated to be aided by the occurrence of surface pre-melting and hence, controlled by capillary forces. Beneficial utilisation of capillary forces through the hierarchical architecture of ceramic powders comprising nanoparticles is an essential feature of this invention. The hierarchical architecture of nanocrystalline powders of this invention is specifically engineered to 1) aid consolidation of particulates into green shape; 2) take advantage of capillary effects during sintering (i.e. liquid phase sintering and surface melting of nanoparticles) to maximize particle rearrangement, enhance sintering kinetics and lower the sintering temperature; and 3) control the size, distribution and morphology of the residual porosity.

Examples of metallic powders useful herein include, but are not limited to Si, Al, Mg, Zr, Y, Ce, Ta and mixtures thereof. These metals are primarily chosen because they oxidize easily and form glass-forming oxides $SiO_2$, $Al_2O_3$, $MgO$, $ZrO_2$, $Y_2O_3$, $CeO_2$ and $Ta_2O_5$ that facilitate liquid-phase formation during sintering. Most of these oxides are currently used as sintering aids or dopants in the manufacture of high-performance ceramics such as alumina, zirconia, silicon nitride and SIALON ceramics. The advantage of adding these elements in metallic rather than oxide form is that as nanophase metal particles they are extremely reactive, have high enthalpy of oxidation, i.e., generate highly localized heat upon oxidation, and provide good coupling for microwave energy.

Examples of ceramic nanocrystalline powders useful herein include, but are not limited to, oxide ceramics such as various forms and modifications of zirconia, alumina, titania, silica, magnesia, yttria, ceria and solid solutions or mixtures thereof.

The metallic powders and ceramic nanocrystalline powders of the present invention have sintering temperatures lower than about 1300° C. and preferably lower than about 1200° C. and most preferably not exceeding about 1100° C. Sintering temperatures of lower than 1300° C. are the most economical since sintering can be carried out in the most common resistance-heated furnaces having metallic heating elements. Each dental lab has at least one burn-out furnace with a maximum continuous operating temperature of at least 1100° C. and a porcelain furnace with a maximum operating temperature of about 1200° C. The essential feature of this invention is that these powders can be processed into dental restorations using both the most sophisticated state-of-the-art technologies such as Solid Free Form Manufacturing (SFF) methods, also known as Rapid Prototyping (RP), as well as manual techniques similar to classic methods of building porcelain jacket crowns on a refractory die, or jacket crowns made using tape-cast sheets or slip casting a ceramic slip on a porous mold. Examples of SFF/RP methods include stereo-lithography (SLA) and photo-stereo-lithography including Digital Light Processing (DLP) and Rapid Micro Product Development (RMPD) mask technique, selective laser sintering (SLS), ballistic particle manufacturing (BPM), fusion deposition modeling (FDM), multi-jet modeling (MJM) and three-dimensional printing (3DP).

Figure 2:
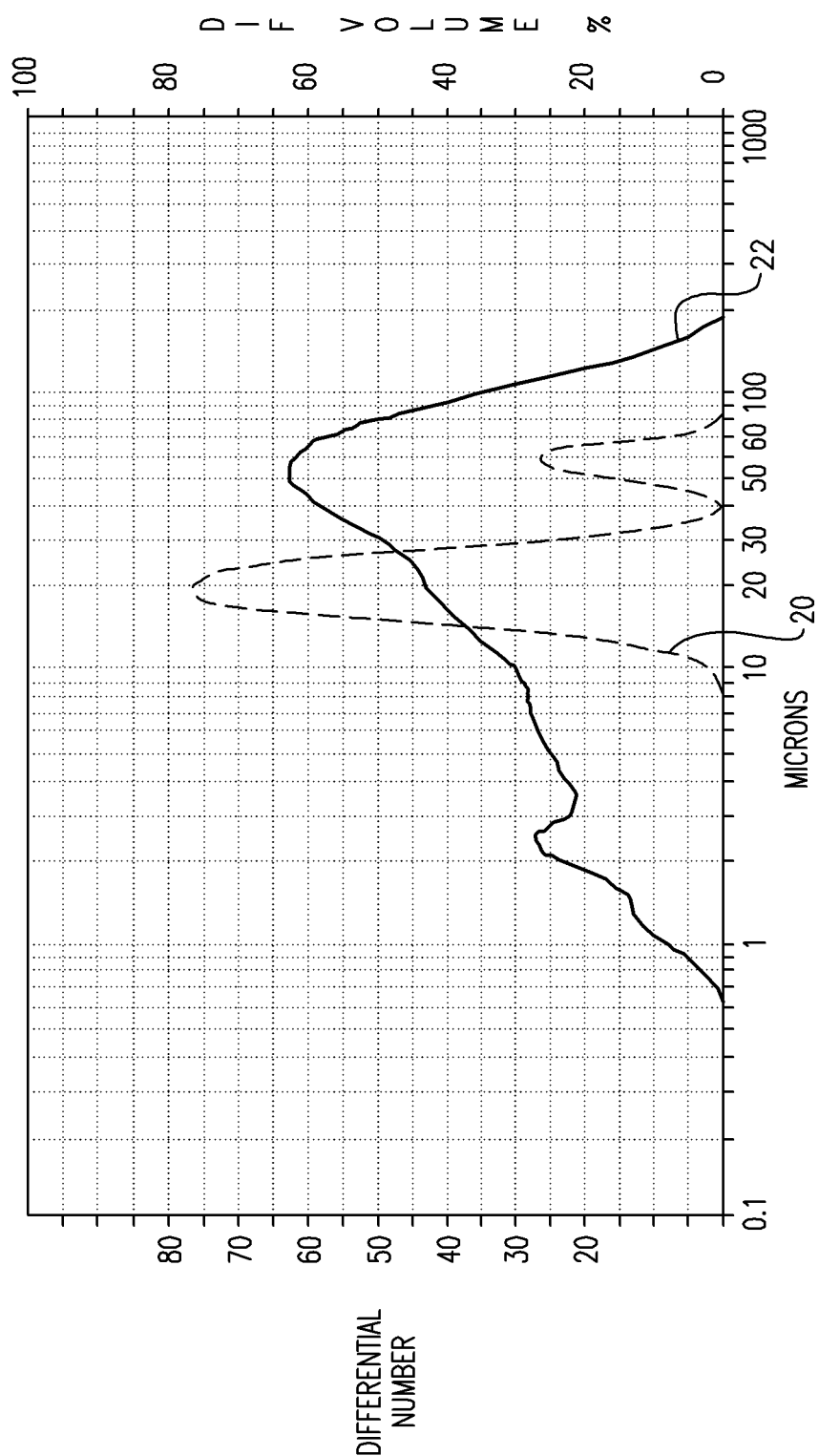
FIG. 2 is a schematic diagram showing particle size distribution of ceramic powders.

Particle size distribution of these powders made of granules and polycrystalline particles is designed to improve handling for making restorations by hand or to optimize powder bed or feed-stock characteristics for specific SFF methods used. Engineered particulate materials of the present invention have complex hierarchical architecture with three levels of structural organization: nano-, micro-, and macro-level as shown in FIG. 1. On the macro-level the particulates are formed into a nearly spherical shape with a diameter from about 10 microns to about 500 microns, more preferably from about 20 to about 200 microns. These spherical particles should preferably be solid, not hollow. The size distribution of powders useful herein should be optimized for the specific forming technique. For example, for building by hand, the particle size distribution should be bimodal with the fraction of finer particles fitting in the interstitials between the fraction of coarser particles. The ratio of the mean diameter of coarser particles ($D_c$) to the mean diameter of finer particles ($D_f$), $D_c/D_f$, should be more than 3 and preferably more than 6, whereas the relative amount of finer particles is from about 10 wt % to about 25 wt %. An example of particle size distribution is shown in FIG. 2. Curve 20 depicts particle size distribution of nanophase powder facilitating manual build-up and curve 22 depicts typical volume based distribution for dental porcelain with good "handling."

In addition to using nanocrystalline powders to induce low sintering temperatures, sintering aids and binders/additives may be mixed with the nanocrystalline powders to further facilitate the action of capillary forces to aid in powder consolidation and sintering. Binders used herein may include any known binder used in conventional powder processing methods and may be compounds or mixtures of compounds activated by heat, light, or other types of radiation or by chemical reaction. Examples of binders/additives include, but are not limited to, polymeric binders, plasticizers, surfactants and dispersants such as polyacrylic binders, polyvinyl alcohol (PVA) binders, polyvinyl butyral binders, stearic and oleic acids, silanes, and various natural and synthetic waxes such as paraffin wax, polyethylene wax, carnauba wax, and bee's wax.

In accordance with a method herein, ceramic powder comprising nanocrystals is mixed with a metallic sintering aid comprising metallic micro- and/or macro-size particles. Other sintering aids and binders may also be added to the mixture. During mixing, the nanocrystalline powders become coated with the additives using any of the available coating/agglomeration techniques including, but not limited to, spray drying, fluidized bed agglomeration methods, dry and wet milling and mechanical alloying. In one of the preferred embodiments of the present invention, the additives comprise metallic particulates. In another embodiment, the additives comprise ceramic nanophases and/or nanocrystallites such as grain growth inhibitors. These sintering aids/additives facilitate the thermal sintering/densification process.

After mixing, the mixture is then sintered at a temperature of less than about 1300° C., preferably at a temperature of less than about 1200° C. and most preferably in the range of temperatures from about 800° C. to about 1150° C.

In yet another embodiment, microwave processing is used to densify the particulate by sintering through the absorption of microwave energy.

Processes occurring during the melting of a material comprising nanoparticles as described above are somewhat similar to the processes occurring during liquid phase sintering as described in Fundamentals of Ceramics, M. Barsoum, McGraw Hill (1997). In both cases, the defining factor is the presence of liquid and therefore the entire process is controlled by capillary forces. In contrast however, during liquid phase sintering the liquid phase is formed due to the addition of sintering aids, and during the sintering of nanoparticles, formation of the liquid skin on nanoparticles occurs by the mechanism of surface melting, intrinsic to nanophase materials. This invention takes advantage of both intrinsic liquid formation (due to surface melting of nanoparticles) and extrinsic liquid formation (due to sintering aids). The nanocrystalline structure of the polycrystalline particles are combined with sintering aids when they are agglomerated into granules. The granules themselves are coated with a coating comprising sintering aids and agents to aid capillary forces during sintering as well as in the forming of the shape. For example, handling of the powder/liquid paste-like mixture for manual wet-condensing of ceramic powder on a refractory die is primarily controlled by capillary forces.

Particulate material comprised of nanoparticles may behave in ways similar to glass-ceramic material due to a very significant fraction of relatively disordered material on grain boundaries. In addition, extremely high specific surface energy associated with nanoparticles greatly increases the driving force for densification. A high fraction of grain boundaries substantially alters sintering behavior of nanosized ceramics compared to that of conventional micronsized ceramics. Surface melting of nanoparticles, resulting in liquid skin formation around nanoparticles, induces and promotes the mechanisms of sintering previously associated with liquid phase sintering such as particle rearrangement and solution-precipitation. At the same time, grain-boundary diffusion sintering mechanisms are greatly enhanced due to the enormous surface area of the nanoparticles. Normally, the presence of agglomerates inhibits densification during solid-state sintering, however, with added mechanisms of liquid phase sintering and surface melting of nanoparticles, deliberate granulation of powder is an essential feature of this invention that facilitates beneficial capillary effects during green shape fabrication and sintering.

It is expected that hand-built restorations will have some residual porosity after final sintering, however, the architecture of the powder is designed to minimize this residual porosity and spatially coordinate it to minimize its adverse effect on mechanical properties. It is now recognized that porosity is practically an unavoidable element of microstructure and porous ceramics are not necessarily weak, as stated in "Fracture Energy of an Aligned Porous Silicon Nitride," by Y. Inagaki, T. Ohji, S. Kanzaki and Y. Shigekaki, *J. Am. Ceram. Soc.*, 83 (7), 1807-1809, (2000). Porosity as an engineered element of the microstructure of the materials of the present invention can be controlled and spatially organized through engineered hierarchy of the starting particulate material. It is well known in the art that the critical flaw size causing brittle fracture of ceramics often scales with the particle size of the starting powder. In materials of the present invention, the powder is preferably spherical in shape promoting better flowability of the powder. In the powder herein, the pore size scales with the diameter of interstitial sites formed between the particles of the powder providing that the powder was carefully condensed or compacted and attained the maximum green density of the compact. The pore size and spatial distribution will be defined by the size and spatial distribution of interstitials between the particles. For example, for a spherical powder with particle size distribution shown in curve 1 of FIG. 2 the largest pore diameter will be defined by the size of the largest interstitial between the smallest spherical particles, which in this case is about 20 μm. The largest, octahedral interstitial in close packed arrangement of 20 μm spheres will be $(\sqrt{3}-1)$ μm×20=0.732×20 μm=14.64 μm.

The equation $\sigma = K_{IC}/(Ya^{1/2})$ calculates the strength based on the value of fracture toughness and the critical flaw size, where $K_{IC}$ is the fracture toughness;
Y is the geometric factor;
σ is the fracture strength;
$\sqrt{}$ is the square root; and
2a is the equivalent crack length associated with the critical flaw.

For a yttria-stabilized tetragonal zirconia polycrystals (YTZP) material with $K_{IC}$ of 6-9 MPa·m$^{1/2}$, and a geometric factor (Y) of 2, strength will most likely be well in excess of 700 MPa.

TABLE 2

| $K_{IC}$, MPa·m$^{1/2}$ | Largest Pore Size, μm | Y* (1.84-2.46) | Strength, MPa |
|---|---|---|---|
| 6 | 15 | 2 | 775 |
| 9 | 15 | 2 | 1162 |

Nanocrystalline particulate ceramic materials of this invention are supplied as free-flowing powder, pre-sintered blanks, feed-stock (for injection molding) and suspensions for slip-casting or electroforming and using fabrication techniques described below to provide materials with flexure strength of at least 700 MPa and exceeding 1 GPa which is more than enough even for multi-unit posterior restorations and cantilever bridges.

The following examples illustrate the invention.

Example 1

Commercially available TZ-3Y-E (which is a yttria-stabilized tetragonal zirconia powder) powder manufactured by TOSOH Corporation (Japan) with a crystallite size of about 30 nm can be sintered to full density at temperatures as low as 1350° C., which is 150° C. lower than the sintering temperature for conventional yttria-stabilized tetragonal zirconia polycrystals (YTZP) powder. Onset of sintering normally occurs at about 0.6 of the melting point (Tm) and the MPD effect described above results in a corresponding decrease in sintering temperature for nanopowder compared to conventional micron-size ceramic. If the size of the crystallites is reduced three times to about 10 nm, the anticipated reduction in the sintering temperature will be about 450° C., i.e., YTZP powder comprised of 10 nm nanoparticles is sinterable at about 1050° C. Thus, this powder may be sintered in a regular burn-out furnace with the maximum operating temperature of 1100° C. Example 2 below further illustrates the viability of sintering nanosized zirconia powders to nearly full density at temperatures lower than 1300° C. and preferably lower than 1100° C.

Example 2

Low Temperature Sinterability of Nano-Zirconia Powders

Two commercially available nano-sized 3 mol % yttria stabilised zirconia powders were obtained from NanoProducts Corporation (Longmont, Colo. 80504, USA). The physical characteristics of these powders are listed in Table 3. Also listed are the properties of TZ-3YS-E powder available from Tosoh Corporation (Tokyo, Japan), a conventional so-called "easy sintering" 3 mol % yttria-stabilized tetragonal zirconia powder that was used for baseline comparison. The nano-powders were mixed with 5-10 wt. % PVA binder (Elvanol 50-42, Dupont) with a mortar and pestle, and then sieved through an 80 mesh screen resulting in free-flowing, pressable powder. The conventional zirconia powder was pressable to begin with, as it contained binder.

Figure 3:
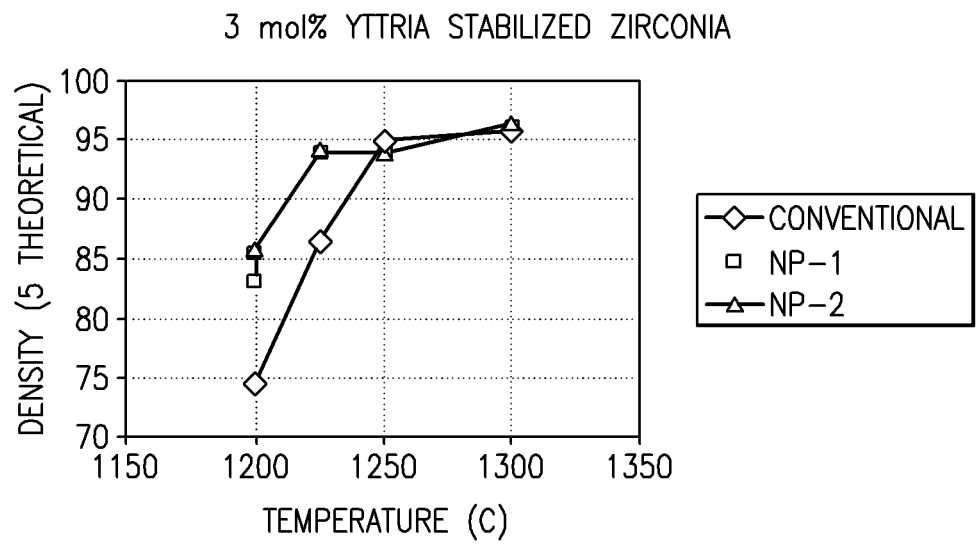
FIG. 3 is a graph showing density versus sintering temperature of nano-sized and conventional three mole percent yttria-stabilised zirconia.

The powders were pressed into pellets using a double action die and then vacuum bagged and cold isostatically pressed (CIPed) at 400 MPa to remove any green density gradients. The resulting pellets were approximately 3 grams in weight and measured about 12 mm in diameter and about 7 mm in height. The green density of conventional and nanosized zirconia pellets were approximately the same, 54±0.2% and 52.6±1.2%, respectively. The pellets were then burned out by heating at a rate of 2° C./m to 700° C. and holding for 2 hours. The pellets were subsequently sintered at 1200-1300° C. for 2 hours with a heating and cooling rate of 4° C./m. Density of the sintered pellets was measured by the Archimedes method using water as the immersion medium. The percent theoretical density was calculated using a theoretical density value of 6.05 g/cm$^3$. These results are shown in FIG. 3 and demonstrate that at temperatures below 1250° C., the nano-sized zirconia samples exhibit enhanced sintering behavior at lower temperatures versus the conventional zirconia sample. For example at 1225° C. the NP-2 pellets densified to 94.1±0.2% which compares to 86.5±0.2% for the conventional zirconia sample. This improved sintering behavior is attributed to the smaller crystallite and particle size of the NP-1 powder (see Table 3). This sintering enhancement due to smaller crystallites/particles is also reflected by the data at 1200° C., which shows a progressive increase in density from the conventional zirconia sample (74.5±0.3%) to the nanoparticulate zirconia samples, NP-1 (83.1±0.1%) and NP-2 (85.8±0.1%). To reduce sintering temperatures below 1000° C. the average particle size should be reduced to below about 8 microns as demonstrated by Kimel and Skandan et al. (cited above).

TABLE 3

| Powder | Crystallite Size (nm) | Particle Size (nm) | Specific Surface Area ($m^2/g$) |
|---|---|---|---|
| NP-1; NanoProducts Corp. (Longmont, CO, USA) product number ZR3N3063 | 10.2 | 17.2 | 59.6 |
| NP-2; NanoProducts Corp. (Longmont, CO, USA) product number ZR3N3269 | 8.8 | 15.3 | 67.1 |
| Conventional 3Y-Zirconia; Tosoh product TZ-3YS-E | 36 | 90 | 7 ± 2 |

Example 3 further illustrates that some of these nanopowders can be sintered isotropically using simplified cup shape geometry.

Example 3

Figure 4:
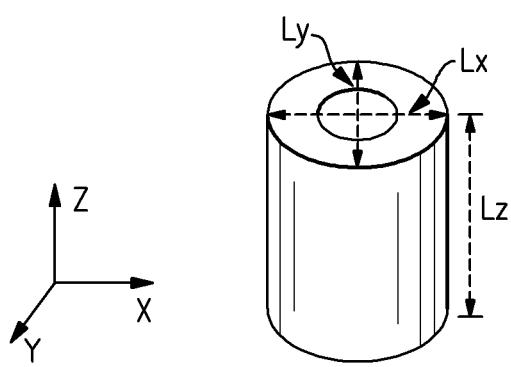
FIG. 4 is a schematic diagram of sample geometry and an orthogonal coordinate system used for sintering shrinkage measurements.
Figure 5:
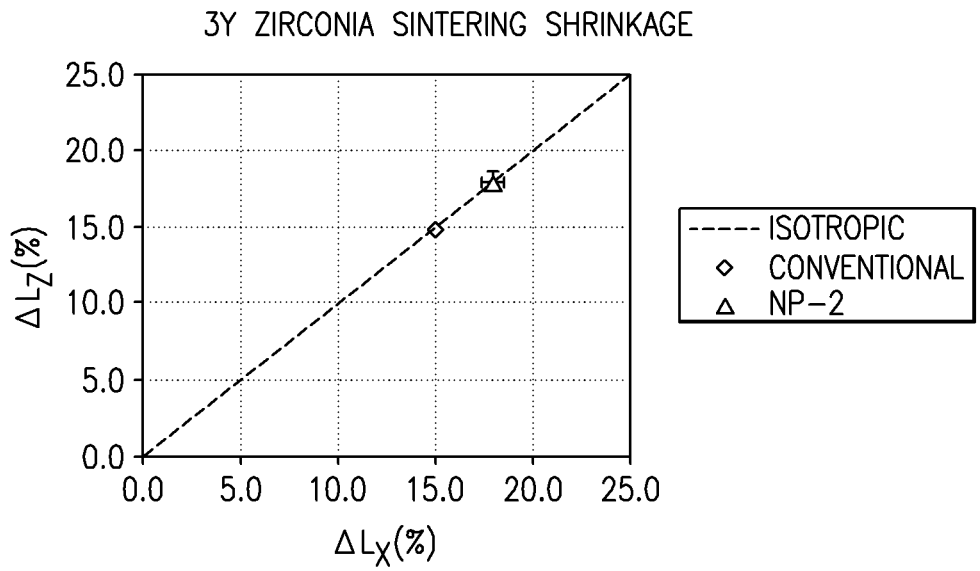
FIG. 5 is a graph showing shrinkage of outside diameter $L_x$ versus shrinkage of the height of cups made out of conventional zirconia powder and nanosized zirconia powder (NP-2)
Figure 6:
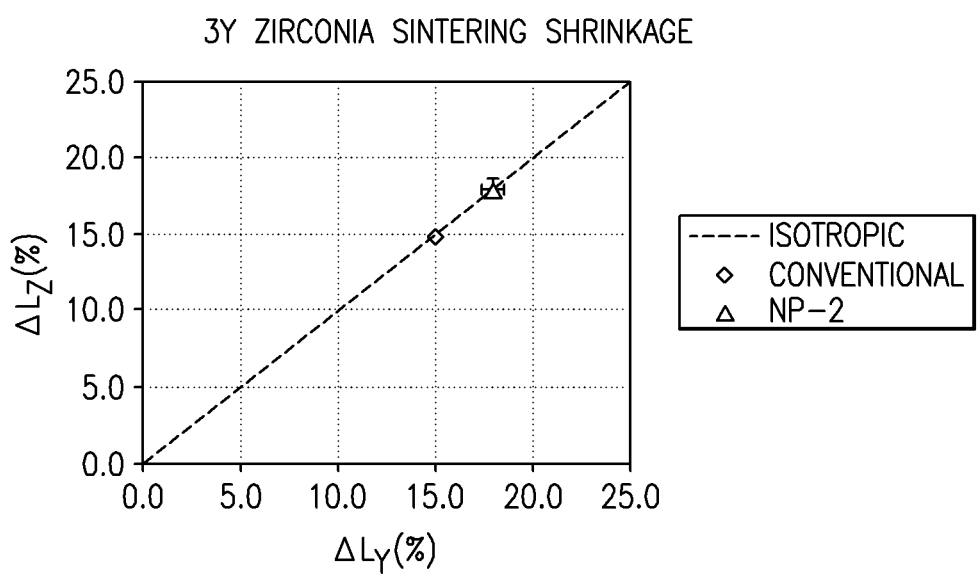
FIG. 6 is a graph showing shrinkage of outside diameter $L_y$ versus shrinkage of the height of cups made out of conventional zirconia powder and nanosized zirconia powder (NP-2).

Using the methods described in example 1, green cylindrical shaped bodies with dimensions of ~12 mm diameter by ~12 mm height were formed out of the NP-2 and conventional zirconia powders. A 5 mm diameter×8 mm deep hole was machined into the green bodies yielding a "cup" geometry. This geometry was chosen since it simulated a dental coping. After recording the orthogonal dimensions, $L_{(x,y,z)}$ where x and y refer to the diameters taken at a 90° rotation to each other and z refers to the height as illustrated in FIG. 4, the green bodies were burned out by heating at a rate of 2° C./m to 700° C. and holding for 2 hours, and subsequently sintering at 1225° C. for 2 h with a heating and cooling rate of 4° C./m. The dimensions of the sintered bodies were recorded and the sintering shrinkage was calculated. These results are shown in FIGS. 5 and 6. These data show that greater shrinkages were achieved for the nanosized zirconia powder versus the conventional zirconia, which agrees with the sintering results shown in Example 2. Additionally, as manifested by the data points falling on the line of isotropic shrinkage represented by the dashed lines, these results demonstrate that like the conventional zirconia the nanosized zirconia also densifies and shrinks isotropically during sintering.

Example 4

Commercially available nano-sized alumina powder AL3N3197 obtained from NanoProducts Corporation (Longmont, Colo. 80504, USA) was premixed into NP-2 zirconia nanopowder used in Examples 2 and 3 above. The physical characteristics of alumina nano-powder are compared to NP-2 below:

TABLE 4

| Powders from NanoProducts Corp. (Longmont, CO, USA) | Composition | Crystallite Size (nm) | Particle Size (nm) | Specific Surface Area ($m^2/g$) |
|---|---|---|---|---|
| NP-3 (product # AL3N3197), $Al_2O_3$ nanopowder | 99.9% $Al_2O_3$ | 4.3 | 8.6 | 175.2 |
| NP-2 (product # ZR3N3269) YTZP nanopowder | 94.7% $ZrO_2$ + 5.3% $Y_2O_3$ | 8.8 | 15.3 | 67.1 |

The blend of 0.5 wt % of NP-3 and 99.5 wt % of NP-2 nano-powders was mixed with 5-10 wt % PVA binder (Elvanol 50-42, Dupont) with a mortar and pestle, and then sieved through an 80 mesh screen resulting in free-flowing, pressable powder. The powder was vacuum bagged and cold isostatically pressed at 400 MPa to produce green billets of about 1-2 inches in diameter and about 5-10 inches in length. Following the cold isostatically pressing step, the outer layer of the billets were removed by turning to eliminate any green density gradients that may have existed in the outer layer. The billet was further sectioned into shorter cylinders of about 30 mm in diameter and about 50-60 mm in height. The cylinders were then debinderized and pre-sintered to about 50% theoretical density in a two step firing cycle comprising heating at the rate of 1° C./minute to about 700° C. and holding for about 2 hours at this temperature followed by a 2 hour hold at about 900° C. The attained bisque densities and the anticipated Bisque-to-Final linear shrinkages were calculated for each individual block based on diameter and height measurements before and after pre-sintering.

The pre-sintered cylinders are subsequently used to mill the enlarged frameworks for dental restorations. Each framework is enlarged based on the linear shrinkage factor calculated for each individual pre-sintered cylinder from which the framework is milled. The milled frameworks are sintered at 1250° C. for 4 hours with a heating rate of 2° C./minute to densities exceeding about 95% theoretical density as determined by the Archimedes method. The isotropic shrinkage in the frameworks is confirmed by fitting frameworks on the original master model. Some of the frameworks were layered by 3G Porcelain (Pentron® Laboratory Technologies, LLC, Wallingford, Conn.) to demonstrate the finishing steps typical in fabrication of aesthetic all-ceramic dental restorations.

The examples above demonstrate that the selected nano-sized powders exhibiting sinterability below 1300° C. were consolidated into shapes that were sintered isotropically, i.e. without distortion wherein $$L_x = L_y = L_z = L_{Diameter} = L_{Height}$$

where L is the linear shrinkage. It was observed that sintering of the compacts of the nanopowders capable of isotropic sintering results in nearly fully densified articles with the average grain size noticeably larger than 100 nm. Two major difficulties in processing dental articles using nanopowders were revealed: (1) the consolidation of bulk shapes by conventional methods such as powder compaction and slip-casting; and (2) sintering to achieve densities in excess of 95%.

To overcome the first processing obstacle mentioned above, solid free form manufacturing methods such as rapid prototyping or solid imaging are utilised indirectly in combination with other processing techniques such as injection molding/heat-pressing, various coating or deposition techniques such as gel casting, slip casting, slurry casting, pressure infiltration, dipping, colloidal spray deposition, direct coagulation as described in U.S. Pat. Nos. 5,667,548, 5,788,891 and 5,948,335, which are hereby incorporated by reference, and electroforming or electrophoretic deposition techniques. While SFF methods are used to fabricate enlarged substrates, dies and molds, any of the above listed techniques can be used to form nanoparticulate materials of these invention into green shapes conforming to these substrates or molds. The electroforming is a preferred method since it utilises suspensions which are particularly beneficial for the nanomaterials herein described. Many of the nanoparticulate materials described herein are more readily obtained as well-dispersed suspensions rather than free-flowing powders. Example 5 illustrates electroforming as the preferred method of depositing ceramic nanoparticulates onto enlarged dies produced by one of solid free form manufacturing methods. Yet another preferred technique is low-pressure injection molding into negative molds of the rapid prototyped models, or alternatively existing heat pressing equipment can be used for pressing into refractory investment molds produced by lost wax technique. Example 6 illustrates low-pressure injection molding as another preferred method of forming ceramic nanoparticulates using enlarged molds produced by one of SFF methods.

To alleviate the second processing obstacle mentioned above, the nanopowders herein are agglomerated with sintering aids such as Si, Al, Mg, Zr, Y, Ce, Ta and mixtures thereof, and grain growth inhibitors such as Cr, Ti, Ni, Mn and mixtures thereof. Depending on the subsequent processing steps, these additions can be added in their elemental (metallic) form or in the form of oxides, salts, organometallic compounds, or other precursor compounds, in the form of colloids, powders and specifically nanopowders. To further lower the melting temperature, the inclusion of the above-mentioned additives as nanopowders or precursor compounds, is most preferred.

Example 5

An optical scanner, ZFN D-21, available from ZFN (Zahntechnisches Fraszentrum Nord GmbH & Co. KG, Warin, Germany) is utilised to scan master models (dies) made from impressions comprising preparations for bridges and crowns. Three-dimensional CAD software provided with a ZFN D-21 scanner is used to design frameworks and copings corresponding to these master models (dies). 3D CAD files (solid models) of these frameworks and copings are enlarged using the linear shrinkage coefficient corresponding to the anticipated sintering shrinkage of the nanozirconia materials of the present invention, saved as stereolithography (.STL) files and transferred to a computer interfaced with an RP (Rapid Prototyping) machine such as Perfactory® Mini available from Envision Technologies GmbH (Marl, Germany). This machine utilises a photostereolithography process also known as digital light processing (DLP) to build three-dimensional objects from a light curable resin. Fifteen units are built at the same time layer by layer with an individual layer thickness of about 50 microns. Individual units are separated, attached to copper wire electrodes and coated with conductive silver paint (silver lacquer) available from Gramm GmbH or Wieland Dental+Technik GmbH & Co., KG (Pforzheim/Germany). AN electroforming unit, such as AGC® Micro Plus (Wieland Dental+Technik GmbH & Co. KG), is used to deposit a dense layer of yttria-stabilised zirconia polycrystals (YTZP) from an ethanol based suspension as described in Example 3 of U.S. Pat. No. 6,059,949, which is hereby incorporated by reference. An electroforming suspension is prepared by suspending NP-2 zirconia powder available from NanoProducts Corp. (Longmont, Colo.) in pure ethanol with addition of 0.05% vol. acetyl acetone dispersant and 0.1% vol. of 5% wt. PVB (polyvinyl butyral binder) in pure ethanol. Alternatively, an ethanol-based suspension is prepared from an aqueous suspension comprising tetragonal nano-zirconia particles of about 8 nm average particle size. First, aqueous suspensions of YTZP having a crystal size of about 8 nm are prepared via precipitation from homogeneous solutions using complexation chemistry techniques. Zirconium and yttrium salts, $ZrO(NO_3)_2 \cdot xH_2O$ (zirconyl nitrate, Aldrich Chem., Milwaukee, Wis.) and $Y(NO_3)_3 \cdot 6H_2O$ (yttrium nitrate hexahydrate), Aldrich Chem., Milwaukee, Wis.) are each dissolved in $CO_2$-free deionized water in the appropriate amounts to achieve 0.5 M solutions of each. These are then mixed, in the appropriate ratio to yield the desired mol. % of $Y_2O_3$ in the final powder, with the complexing agent bicine (www.sigmaaldrich.com) (2:1 bicine:Zr (mol)). The pH of this feed solution is adjusted to about 13 by additions of TEAOH (Tetraethylammonium Hydroxide, Aldrich Chem., Milwaukee, Wis.), and the solution is then put in a teflon-lined hydrothermal vessel (Parr Instrument Company, Moline, Ill.), which is heated to 200° C. for 8 hours to hydrothermally synthesize YTZP crystals of about 8 nm in size.

Aqueous suspensions are converted into alcohol-based suspensions by centrifuging and then redispersing in ethanol. The average thickness of the electrophoretic coating is about 0.5-0.6 mm. Following electroforming of the powders onto the substrates, sintering is carried out in a Deltech furnace using a two-step firing cycle comprising heating rate of 1° C./min to about 450° C., holding at this temperature for 2 hours to remove organics, further heating at a rate of 1° C./min. to 900° C.-1100° C. and holding at this temperature for about 2 hours. Densities in excess of 90% of theoretical density can be achieved.

Example 6

Low-Pressure Injection Molding (LPIM) with Peltsman Unit

An optical scanner, ZFN D-21, available from ZFN (Zahntechnisches Fraszentrum Nord GmbH & Co. KG (Warin, Germany) is utilised to scan master models (dies) made from impressions comprising preparations for bridges and crowns. 3D CAD software provided with a ZFN D-21 scanner is used to design frameworks and copings corresponding to these master models (dies). 3D CAD files (solid models) of these frameworks and copings are enlarged using the linear shrinkage coefficient corresponding to the anticipated sintering shrinkage of the nanozirconia materials of the present invention, saved as stereolithography (.STL) files and transferred to a computer interfaced with an RP (Rapid Prototyping) machine such as Perfactory® Mini available from Envision Technologies GmbH (Marl, Germany). This machine utilises photostereolithography process also known as digital light processing (DLP) to build 3D objects from a light curable resin. Fifteen units are built at the same time layer by layer with an individual layer thickness of about 50 microns. Individual units are separated and molded in a liquid silicone rubber (Silastic® M RTV Silicone Rubber from Dow Corning Corporation) which is castable and easily demolded after curing to produce negative molds for low-pressure injection molding. It should be noted that instead of using silicone negative molds, the molds for LPIM can be designed and fabricated directly using the Perfactory® Mini RP machine and the supplied software.

Feedstock containing nanosized zirconia for injection molding is prepared from a binder comprised of 75 wt % of paraffin wax (melting point of 49°-52° C.), 10 wt % of polyethylene wax (melting point of 80°-90° C.), 10% of carnauba wax (melting point of 80°-87° C.), 2 wt % of stearic acid (melting point of 75° C.) and 3 wt % of oleic acid (melting point of 16° C.) readily available from a number of suppliers. Nano sized zirconia having a crystallite size of about 19 nm and particle size of about 15 nm (available as Product Number ZR3N3269 from NanoProducts Corp., Longmont, Colo. 80504, USA) is used. The mixing is done directly in a low pressure molding (LPM) machine, (Model MIGL-33 available from Peltsman Corporation, Minneapolis, Minn.) at a temperature of 90° C. The feedstock mixture is comprised of about fifty percent (50%) by volume of a binder. Once the feed stock mixture is thoroughly mixed it is injected into the cavity of the silicone rubber molds at a pressure of approximately 0.4 MPa and a temperature of approximately 90° C. The injection-molded green part is then demolded from the silicone mold, which is done easily due to elasticity of the silicone. Green densities of approximately 50% were achieved. The green bodies were debinderized and sintered to nearly full density as described above.

Example 7

Injection Molding with Autopress

Feedstock containing nanosized zirconia for injection molding is prepared from a binder comprised of paraffin wax, with minor proportions of polyethylene wax, carnauba wax, stearic and oleic acids using the same formulation as used in Example 6. Nanosized zirconia having a crystallite size of about 19 nm and a particle size of about 15 nm (available as Product Number ZR3N3269 from NanoProducts Corp., Longmont, Colo. 80504, USA) is used. The mixing is done in a KitchenAid Professional 5 mixer (St. Joseph, Mich.) in a bowl continuously heated to 90° C., which is above the melting point of the binder. Heating is achieved using a high temperature heat tape available from McMaster-Carr (New Brunswick, N.J.). The heat tape is wrapped around the mixer bowl to provide heat to the bowl. After cooling to room temperature, the resulting mix is crushed into powder to a 60 mesh (250 μm) particle size using a mortar and pestle. This powder is then ready for injection into the cavity of a mold. Additionally, the mix can be cast into pellets by pouring into a metal "clam-shell" mold, while still in the molten state.

Previously acquired stereolithography (*.STL) files of bridge frameworks and crown copings were sent to microTEC, Bismarckstrasse 142 b 47057 Duisburg, Germany) for production of the enlarged replicas using RMPD®-mask technology via toll rapid prototyping service available through microTEC's website. The replicas were fabricated in a layer thickness of twenty five microns (25 μm) from photo-curable resin.

The resulting replicas are invested in Universal™ Refractory Investment (available from Pentron® Laboratory Technologies, LLC, Wallingford, Conn.). After the investment has hardened, the resin replicas inside are eliminated by placing it into a preheated furnace thereby burning off the resin, resulting in a mold cavity for forming the dental article. The injection molding feedstock, in free-flowing granule or pellet form, as described above, is then placed into the investment mold assembly, which is then transferred into the pressing unit. It is pressed into the investment ring using an AutoPressPlus® (Pentron® Laboratory Technologies, LLC, Wallingford, Conn.). having an external alumina plunger Pressing is done at approximately 90° C., and after cooling the pressed green part is then carefully divested by sand-blasting with glass beads at a pressure of 15 psi and the plunger and mold are disposed of. Green densities of approximately 50% were achieved. The green bodies were debinderized and sintered to nearly full density as described above.

It should be noted that in all the cases described in Examples 1-7 it was observed that while the ceramic portion of the starting powder, suspension or feedstock consists of crystallites with average sizes of less than 20 nm, the sintered dental articles have average grain sizes within the range from about 100 nm to about 450 nm. It is the nature of the materials of the present invention to exhibit substantial coarsening concurrent with densification wherein the final grain size is about 10-20 times larger than the starting crystallite size.

Though not within the scope of the present invention which is directed towards sintering ceramic dental articles comprising nanopowders to nearly full density, nevertheless, it should be noted that the injection molding technology described in Examples 6 and 7 can be used to produce dental articles even if access to RP machines is not available. In the latter case, if is not possible to make enlarged replicas and green bodies fabricated therefrom as described in Examples 6 and 7, the articles will have to be presintered without shrinkage and glass infiltrated as described in U.S. Pat. Nos. 4,772,436 and 5,910,273, which are hereby incorporated by reference. In the case of YTZP zirconia cores, 3G porcelain (Pentron® Laboratory Technologies, LLC, Wallingford, Conn.) can be used for both glass infiltration and esthetic layering of the resulting glass-infiltrated cores.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of manufacturing a dental article comprising:
    mixing ceramic powder comprising nanoparticles having a crystallite size of less than about 20 nanometers (nm) with a sintering aid comprising metallic particles, wherein the metallic particles have a crystallite size greater than about 100 nanometers;
    forming the powder mixture into a dental article; and
    sintering the article at a temperature of less than about 1300° C.

2. The method of claim 1 wherein the powder mixture is formed into a suspension, slurry, slip, gel, pellet, feedstock material or a pre-sintered blank prior to forming into a dental article.

3. The method of claim 1 wherein the powder mixture is formed into the dental article by injection molding, hot pressing, gel-casting, slip casting, slurry casting, pressure casting, direct coagulation, colloidal spray deposition, dipping, or electroforming.

4. The method of claim 3 wherein the powder mixture is formed into a suspension, slurry, slip, gel, pellet, feedstock material or a pre-sintered blank prior to injection molding, hot pressing, gel-casting, slip casting, slurry casting, pressure casting, direct coagulation, colloidal spray deposition, dipping, or electroforming.

5. The method of claim 1 wherein the powder mixture is formed into the dental article by hand, by CAD/CAM or by rapid prototyping.

6. The method of claim 5 wherein the powder mixture is formed into a suspension, slurry, slip, gel, pellet, feedstock material or a pre-sintered blank prior to forming by hand, by CAD/CAM or by rapid prototyping the dental article.

7. The method of claim 1 wherein sintering the article at a temperature less than about 1300° C. comprises furnace sintering or microwave sintering to densities exceeding 95% of the theoretical density.

8. The method of claim 1 wherein sintering the article at a temperature less than about 1300° C. comprises furnace sintering or microwave sintering to densities exceeding 97% of the theoretical density.

9. The method of claim 1 wherein the sintering the article at a temperature less than about 1300° C. comprises sintering at a temperature less than about 1200° C. to densities exceeding 95% of the theoretical density.

10. The method of claim 1 wherein sintering the article at a temperature less than about 1300° C. comprises sintering at temperature less than about 1100° C. to densities exceeding 95% of the theoretical density.

11. The method of claim 1 wherein the dental article comprises a single component yttria-stabilized tetragonal zirconia.

12. The method of claim 1 wherein the dental article is selected from the group consisting of, bridges, splints, crowns, partial crowns, dentures, teeth, jackets, inlays, onlays, facings, veneers, facets, implants, cylinders, abutments and connectors.

13. The method of claim 1 wherein the sintering aid comprises Si, Al, Mg, Zr, Ce, Ta, oxides thereof, or a combination thereof.

14. The method of claim 1 wherein the dental article shrinks substantially isotropically during sintering.

15. The method of claim 1 wherein the dental article exhibits at least 30% relative transmission of visible light when measured through a thickness in the range of about 0.3 to about 0.5 mm.

* * * * *